United States Patent [19]
Grevis et al.

[11] Patent Number: 5,063,928
[45] Date of Patent: Nov. 12, 1991

[54] APPARATUS AND METHOD FOR DETECTING AND TREATING CARDIAC TACHYARRHYTHMIAS

[75] Inventors: Richard Grevis, Rose Bay; Lorain K. Holley, Waterfall; Philip J. Maker, North Ryde; Geoffrey A. Drane, Annandale; Andrew Parle, Chippendale; Andrew Sands, Marsfield; Rodney Parkin, Mosman; Paul Dyson, Chatswood, all of Australia

[73] Assignee: Telectronics Pacing Systems, Inc., Englewood, Colo.

[21] Appl. No.: 548,056

[22] Filed: Jul. 5, 1990

[51] Int. Cl.$^5$ .............................. A61N 1/362
[52] U.S. Cl. ................... 128/419 D; 128/419 PG
[58] Field of Search .............. 128/419 PG, 419 D

[56] References Cited

U.S. PATENT DOCUMENTS

| | | | |
|---|---|---|---|
| 4,280,502 | 7/1981 | Baker, Jr. et al. | 128/419 PG |
| 4,561,442 | 12/1985 | Vollmann et al. | 128/419 PG |
| 4,577,633 | 3/1986 | Berkovits et al. | 128/419 PG |
| 4,895,151 | 1/1990 | Grevis et al. | 128/419 PG |
| 4,940,054 | 7/1990 | Grevis et al. | 128/419 PG |
| 4,971,058 | 11/1990 | Pless et al. | 128/419 PG |

OTHER PUBLICATIONS

Sowton, E., "Clinical Results with the Tachylog Antitachycardia Pacemaker", Pace, vol. 7, pp. 1313-1317, Nov.-Dec. 1984, Part II.

Warren, J. et al., "Clinical Evaluation of Automatic Tachycardia Diagnosis by an Implanted Device", Pace, vol. 9, pp. 1079-1083, Nov.-Dec. 1986, Part II.

Primary Examiner—William E. Kamm
Assistant Examiner—Scott M. Getzow
Attorney, Agent, or Firm—Gottlieb, Rackman & Reisman

[57] ABSTRACT

An arrhythmia control system and method having automatic determination of the tachycardia confirmation interval. The interval is dynamically set at the minimum of an absolute detection interval and a value calculated as a function of either average sinus interval or tachycardia cycle length or both. The continued presence or the reversion of a pathologic tachycardia can be reliably confirmed, particularly when the patient experiences an elevated heart rate due to, for example, exercise, prior to onset of the tachycardia.

76 Claims, 6 Drawing Sheets

APPARATUS AND METHOD FOR DETECTING AND TREATING CARDIAC TACHYARRHYTHMIAS

BACKGROUND OF THE INVENTION

This invention relates to implantable medical devices which monitor the cardiac state of a patient by sensing sinus rhythm, ventricular tachycardia and ventricular fibrillation and which deliver therapy in the form of electrical energy to cardiac tissue in an attempt to revert tachycardia and restore a normal sinus rhythm.

As used herein, antitachycardia pacing will mean any pacing for the reversion of tachycardia. The term tachycardia refers to any fast, abnormal rhythm of the heart which may be amendable to treatment by electrical discharges and specifically includes ventricular tachycardia (VT), supraventricular tachycardia (SVT), ventricular flutter and/or ventricular fibrillation (VF).

The term therapy as used herein includes the processes used between the detection and reversion of a tachyarrhythmia and includes the actions of antitachycardia pacing, cardioversion and/or defibrillation shocks. The term cardioversion refers to the discharge of electrical energy into the cardiac tissue in an attempt to terminate or revert a tachyarrhythmia. This may take the form of a high energy discharge (up to 40 Joules or more) or a low energy discharge (less than 1 Joule). Cardioversion shocks may or may not be synchronized to the rhythm of the heart. Defibrillation is a particular example of cardioversion.

This invention applies equally to devices which deliver energy synchronized to an R-wave and to those that do not. It also applies to devices which use lower energy pulses (up to 1 Joule) as well as to devices which use higher energy pulses (up to 40 Joules or more). The invention applies to devices which deliver cardioverting shocks alone as well as to devices which deliver antitachycardia pacing pulses alone or in combination with cardioverting shocks. The invention will usually apply to ventricular implantable cardioverters, but is equally applicable to atrial cardioverters or multiple chamber cardioverters or defibrillators. The invention applies also to the delivery of any antitachycardia pacing pulse and post reversion pacing therapy.

BACKGROUND ART

U.S. Pat. No. 4,280,502 to Baker, Jr. et al. describes a method and apparatus for detecting and arresting a condition of tachycardia. In this device, the successive occurrence of a predetermined number of cardiac intervals which are below a preselected tachycardia threshold enables the system to initiate an output to arrest the tachycardia.

Another antitachycardia pacer is disclosed in U.S. Pat. No. 4,561,442 to Vollmann et al. In this device, tachycardia detection is based on the number of times the rate threshold is exceeded before reverting to a normal cardiac cycle. An arrhythmia counter is incremented by one whenever it detects an intrinsic pulse-to-pulse interval shorter than the programmed tachycardia threshold rate and it is decremented by one whenever it detects an interval greater than the threshold interval. Because these devices use only a preselected tachycardia threshold as their means of detection, neither of them can differentiate between sinus tachycardias with pulse intervals shorter than the programmed threshold rate and pathologic tachycardias.

A device which can recognize sinus tachycardia is described in the article "Clinical Evaluation of Automatic Tachycardia Diagnosis by an Implanted Device" by Warren et al. in PACE, Vol. 9, pp. 1079–1083, 1986. A sudden onset criterion is used in combination with a programmed tachycardia threshold to detect a tachycardia. Hence, for a tachycardia to be detected, the first interval to fall below the tachycardia threshold must be shorter than either of the two preceding cardiac intervals by a preset amount. The programmed tachycardia threshold is also used to confirm the continued presence or otherwise of the tachycardia. However, this device, while capable of differentiating between sinus tachycardia and pathologic tachycardia, is not able to detect a pathologic tachycardia which occurs after the heart rate is already elevated as, for example, in the situation of the patient gradually elevating the heart rate while exercising.

Another device which can discriminate between sinus tachycardia and pathologic tachycardia is described in the article "Clinical Results with the Tachylog Antitachycardia Pacemaker" by Sowton in PACE, Vol. 7, pp. 1313–1317 (Nov.–Dec. 1984). In this device, the tachycardia sudden onset detection algorithm becomes activated at some programmable cardiac interval threshold. This cardiac interval threshold is also used to confirm the continued presence or otherwise of the tachycardia. A problem with this device is that while being able to detect a pathologic tachycardia which occurs after the cardiac interval is already less than the cardiac interval threshold, as in an exercise situation, it would have difficulty confirming a successfully reversion of the tachycardia. This is because prior to onset of the pathologic tachycardia, the cardiac interval is shorter than the confirmation interval due to a gradual increase in heart rate in, for example, an exercise situation. It follows that after a successful reversion, the cardiac interval will return to a value near to that prior to onset, that is, to a point which is shorter than the confirmation interval. In this situation, the device does not recognize that the tachycardia has been reverted and it will continue to apply therapy. This can be a traumatic experience for the patient. [It is highly desirable from the viewpoint of patient safety to prevent the delivery of unnecessary therapy.]

There is, therefore, a need for a device which is capable of not only reliably differentiating sinus tachycardias from pathologic tachycardias, but also of reliably confirming either the continued presence or the reversion of a pathologic tachycardia, particularly when the patient experiences an elevated heart rate prior to onset of the tachycardia.

DISCLOSURE OF THE INVENTION

It is an object of the invention to provide an antitachycardia therapy device which reliably detects pathologic tachycardias and distinguishes these from sinus tachycardias induced in a patient, for example, in an exercise situation where there is a gradual increase in heart rate.

It is a further object of the invention to provide an antitachycardia therapy device which reliably detects pathologic tachycardias which occur at elevated heart rates and accurately confirms whether such tachycardias have been reverted by the antitachycardia therapy.

It is a further object of the invention to reduce the likelihood of delivering unnecessary therapy to a patient after a tachycardia has reverted by the automatic calculation of the confirmation threshold based on the conditions prior to and after onset.

According to the invention, there is provided an apparatus for treating cardiac arrhythmias comprising means for continuously measuring the average interval of a predetermined number of sinus intervals; detection means for detecting the presence of a tachycardia including sudden onset detection and an absolute detection interval; antitachycardia therapy means responsive to the detection means for delivering antitachycardia therapy to revert the tachycardia; tachycardia confirmation means for confirming the presence of the tachycardia, the tachycardia confirmation means including a threshold interval detector, means for determining a function of the average sinus interval measured immediately prior to the tachycardia; and means for setting the threshold interval to the lesser value of this function and the absolute detection interval.

There is further provided an apparatus for treating cardiac arrhythmias comprising detection means for detecting the presence of a tachycardia including sudden onset detection and an absolute detection interval; means for measuring the tachycardia cycle length of the detected tachycardia; antitachycardia therapy means responsive to the detection means for delivering antitachycardia therapy to revert the tachycardia; tachycardia confirmation means for confirming the presence of the tachycardia, the tachycardia confirmation means including a threshold interval detector, means for determining a function of the tachycardia cycle length; and means for setting the threshold interval to the lesser value of this function and the absolute detection interval.

In a preferred form of the invention, there is provided a medical device for the reversion of tachycardia. The device includes means for detecting the presence of a tachycardia and means for delivering antitachycardia therapy. The device also includes means for confirmation of the reversion of a tachycardia following the delivery of antitachycardia therapy. The confirmation interval is automatically determined as the minimum value of the absolute detection interval and a function of both the tachycardia cycle length and the average sinus interval prior to the onset of a pathologic tachycardia.

The invention also includes a method of treating cardiac arrhythmias comprising the steps of continuously measuring the average interval of a predetermined number of sinus intervals; detecting the presence of a tachycardia by means of sudden onset detection and an absolute detection interval; delivering antitachycardia therapy responsive to the detecting to revert the tachycardia; confirming the presence of the tachycardia according to the level of a threshold interval; determining a function of the average sinus interval measured immediately prior to the tachycardia detecting; setting the threshold interval to the lesser value of this function and the absolute detection interval; and delivering further antitachycardia therapy responsive to the confirming.

In accordance with the invention there is further provided a method of treating cardiac arrhythmias comprising of the steps of detecting the presence of a tachycardia by means of sudden onset detection and an absolute detection interval; measuring the tachycardia cycle length of the detected tachycardia; delivering antitachycardia therapy responsive to the detecting to revert the tachycardia; confirming the presence of the tachycardia according to the level of a threshold interval; determining a function of the tachycardia cycle length; setting the threshold interval to the lesser value of said function and the absolute detection interval; and delivering further antitachycardia therapy when the presence of the tachycardia is confirmed.

BRIEF DESCRIPTION OF THE DRAWINGS

Further objects, features and advantages of the invention will become apparent upon consideration of the following detailed description in conjunction with the drawings, in which.

DEFINITION OF TERMS

ABSOLUTE CHANGE OF INTERVAL DETECTION (ACID)—A tachycardia detection algorithm which requires a sudden and sustained decrease in sensed cardiac interval, where the required decrease (Delta) is an absolute amount.

ABSOLUTE DETECTION INTERVAL (ADI)—A programmable parameter which determines the level of the cardiac interval above which a tachycardia is absent.

ABSOLUTE INTERVAL DETECTION (AID)—A tachycardia detection algorithm which requires a sustained cardiac interval less than a threshold interval.

AVERAGE SINUS INTERVAL (ASI)—A measure of the normal intrinsic heart interval of the patient. The number of intervals used to determine the average is small enough so that the average can track exercise induced interval changes, but large enough so that it is insensitive to ectopics.

DELTA—A programmable parameter which determines the total interval reduction required for the sudden onset of a tachycardia to be detected when using an ACID or a PCID algorithm.

PERCENTAGE CHANGE OF INTERVAL DETECTION (PCID)—An alternative tachycardia detection algorithm which requires a sudden and sustained decrease in sensed cardiac interval, where the required decrease (Delta) is a percentage of the average sinus interval, that is, for example, Delta=10%×ASI.

TACHYCARDIA CYCLE LENGTH (TCL)—The period of time, or average period of time, between successive sense indications in a tachycardia.

THRESHOLD INTERVAL (TI)—The level which the detected cardiac interval must be equal to or less than for the tachycardia to be confirmed. This level is automatically determined as the lesser value of the absolute detection interval and a function of the average sinus interval, or the tachycardia cycle length, or both.

VERY SHORT INTERVAL DETECTION (VSID)—A tachycardia detection algorithm which detects fast obvious tachycardias, that is, tachycardias where cardiac intervals are less than that attainable by a sinus tachycardia.

BEST MODE FOR CARRYING OUT THE INVENTION

Figure 1:
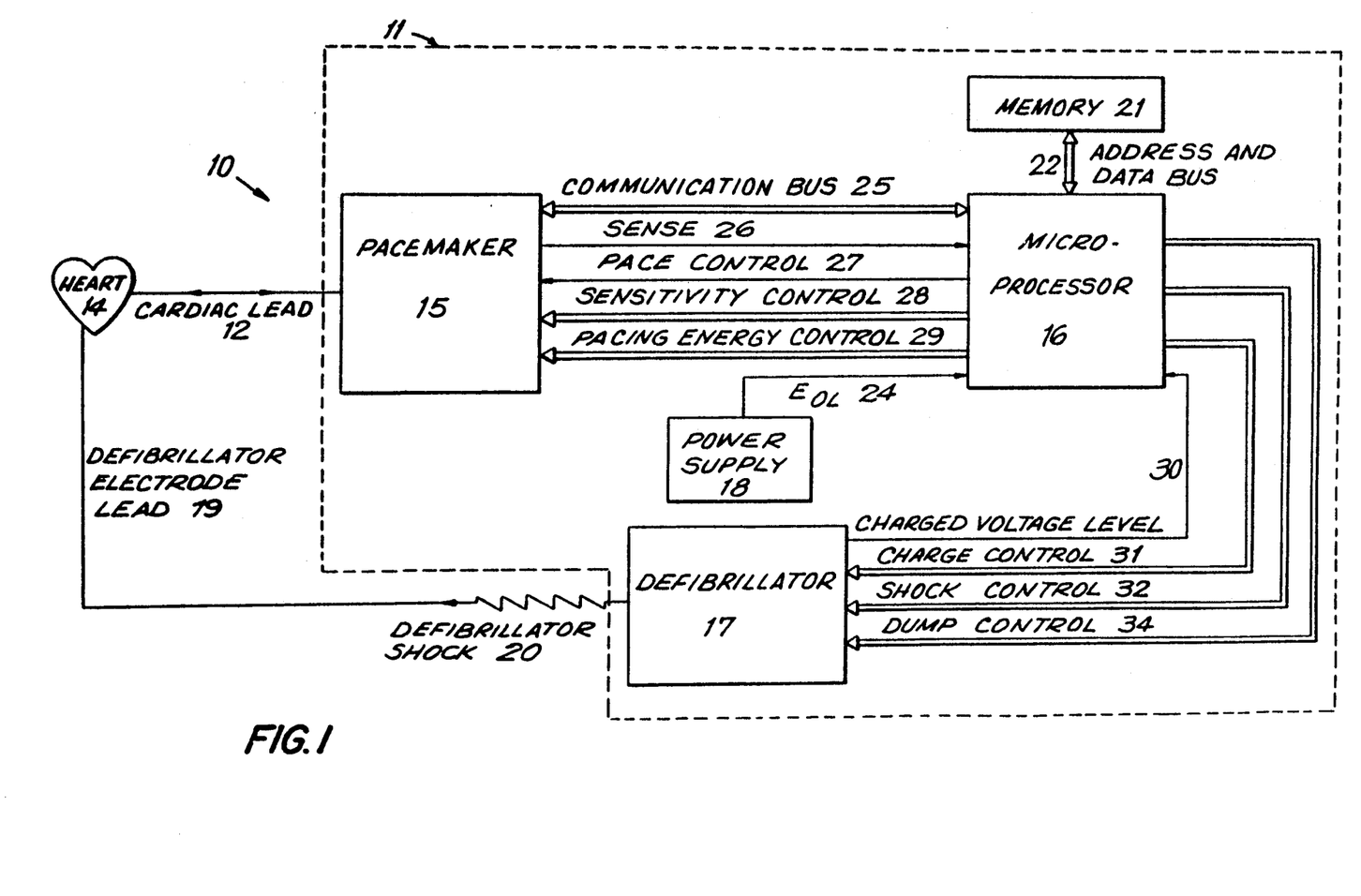
FIG. 1 is a block diagram of an arrhythmia control system (ACS) consisting of a combined microprocessor controlled pacemaker and defibrillator device.

Referring to FIG. 1, there is depicted a block diagram of an arrhythmia control system 10. System 10 is designed to be implantable and includes a pulse module 11 and appropriate leads. More particularly, system 10 will generally include: a cardiac lead 12 connected to the patient's heart 14; a pacemaker 15 for the detection of analog signals representing cardiac electrical activity and for the delivery of pacing pulses to the heart; a microprocessor 16 which, in response to various inputs received from the pacemaker 15 as well as from a defibrillator 17, performs various operations so as to generate different control and data outputs to both pacemaker 15 and defibrillator 17; and a power supply 18 for the provision of a reliable voltage level to pacemaker 15, microprocessor 16 and defibrillator 17 by suitable electrical conductors (not shown). Defibrillator 17 produces a high voltage to charge its capacitors and then discharges them in response to control signals from microprocessor 16. A defibrillator electrode lead 19 transfers the energy of a defibrillator shock 20 from the implanted pulse module to the surface of the heart 14.

Microprocessor 16 is connected to an external memory 21 by an address and data bus 22. An end-of-life (EOL) signal line 24 is used to provide, to microprocessor 16, a logic signal indicative of the approach of battery failure in power supply 18.

As more fully described below, microprocessor 16 and pacemaker 15 are connected by a communication bus 25, a sense line 26, a pace control line 27, a sensitivity control bus 28, and a pacing energy control 29. As also more fully described below, microprocessor 16 is connected to defibrillator 17 by a charge level line 30, a charge control bus 31, a shock control bus 32, and a dump control bus 34.

Figure 2:
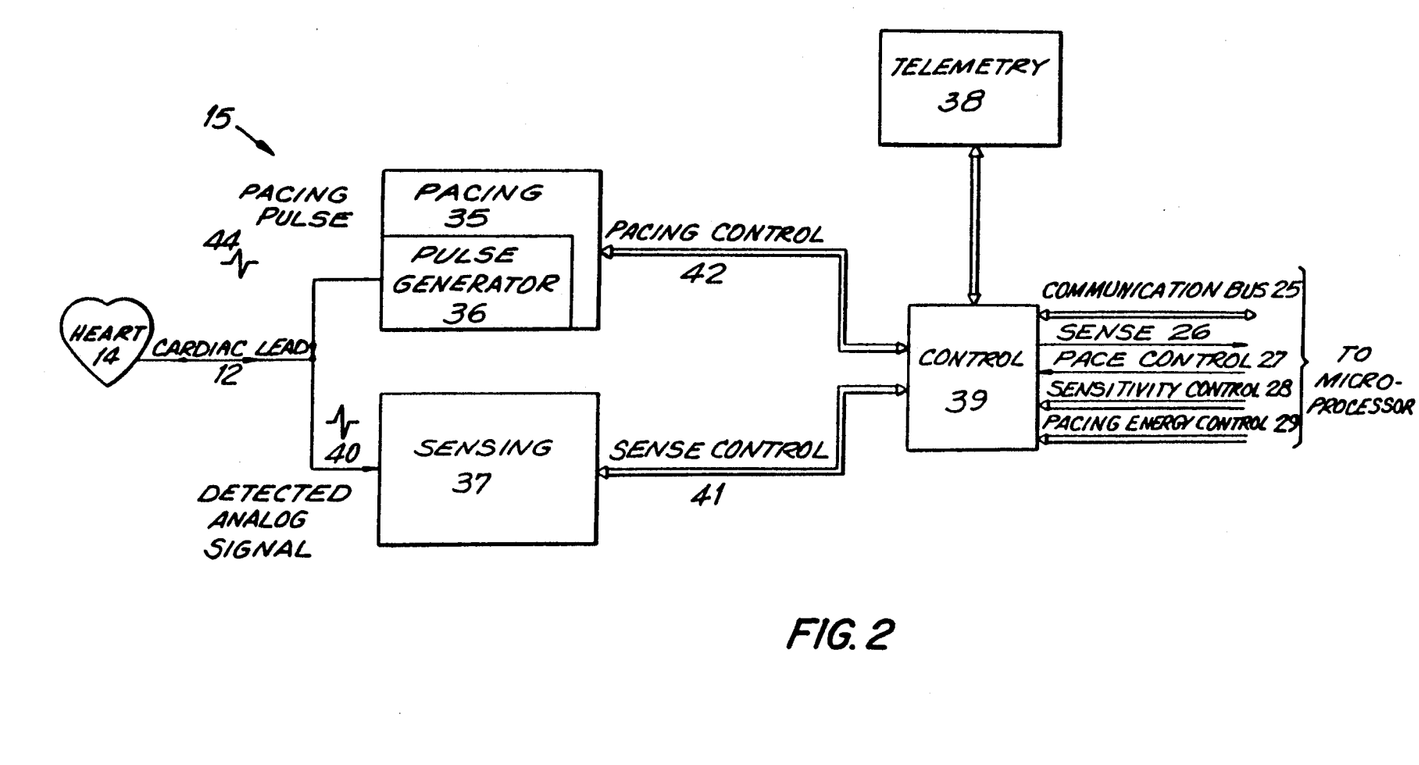
FIG. 2 is a block diagram of the pacemaker of FIG. 1.

Referring to FIG. 2, pacemaker 15 comprises pacing circuit 35 which includes a pacing pulse generator 36, sensing circuit 37, and telemetry circuit 38. In addition, there is a control block 39 which includes an interface to microprocessor 16.

In operation, sensing circuit 37 detects analog signals 40 from the heart 14 and converts the detected signals to digital signals. Furthermore, sensing circuit 37 receives an input sensing control signal (which determines the sensitivity of the detection circuits in sensing circuit 37) by way of a sense control bus 41 from control block 39. A change in this sensitivity will affect the voltage deviation required at the sensing electrode for a sense to be registered. The operation of the logic which changes the sensitivity is described in more detail in U.S. Pat. No. 4,940,054 entitled "Apparatus and Method for Controlling Multiple Sensitivities in Antitachyarrhythmia Device", of Richard Grevis and Norma Louise Gilli, assigned to the assignee of the present invention.

Pacing circuit 35 also receives inputs from control block 39 including a pace control and a pacing energy control by way of pacing control bus 42 which carries the signals on pace control line 27 and pacing energy control bus 29. The pace control determines the type of pacing to occur while the magnitude of the pulse energy is determined by the pacing energy control. Pacing circuit 35 causes pulse generator 36 to generate the pacing pulse 44 which is delivered to the patient's heart 14 by means of cardiac lead 12.

Telemetry circuit 38 provides a bi-directional link between control block 39 of pacemaker 15 and an external device such as a programmer. It allows data such as the operating parameters to be read from or altered in the implanted pulse module 11.

Figure 3:
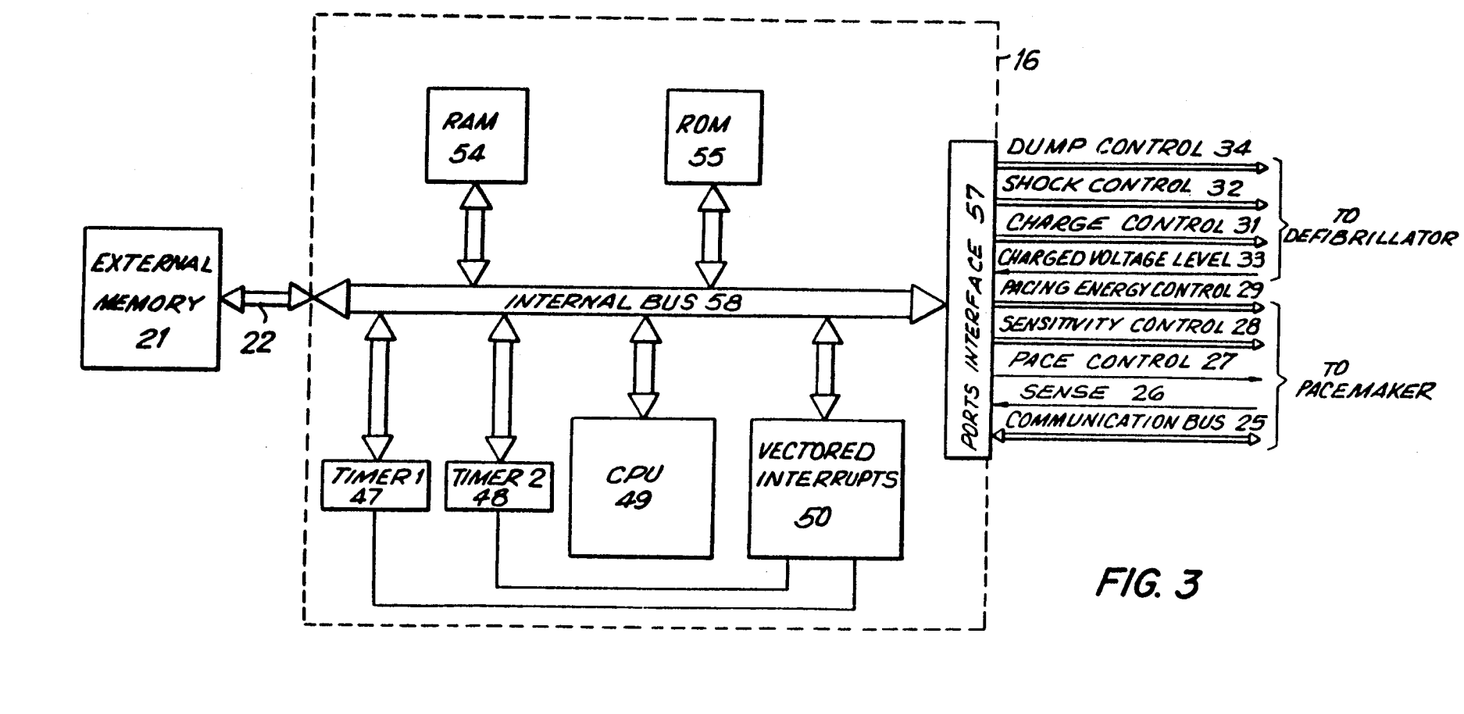
FIG. 3 is a block diagram of the microprocessor of FIG. 1.

Referring to FIG. 3, microprocessor 16 comprises two 16-bit timers 47 and 48, CPU 49, vectored interrupt block 50, RAM 54, ROM 55, ports interface 57 and an internal communications bus 58. RAM 54 acts as a scratch pad memory during execution of the various programs stored in ROM 55 and used by microprocessor 16. These programs include system supervisory programs, detection algorithms, and programming implementing the logic flow diagram of FIG. 4, as well as storage programs for storing, in external memory 21, data concerning the functioning of module 11 and the electrogram provided by cardiac lead 12. Timers 47 and 48 and associated control software implement some timing functions required by microprocessor 16 without resort entirely to software, thus reducing computational loads on and power dissipation by CPU 49.

Signals received from telemetry circuit 38 permit an external programmer (not shown) to change the operating parameters of pacemaker 15 by supplying appropriate signals to control block 39. Communications bus 25 serves to provide signals indicative of such control to microprocessor 16. Thus, it is also possible for an external programmer to control operation of defibrillator 17 by means of signals provided to microprocessor 16.

Appropriate telemetry commands may cause telemetry circuit 38 to transmit data to the external programmer. Data which has been stored is read out, by microprocessor 16, on the communications bus 25, through control block 39 in pacemaker 15, and into control block 38 for transmission to the external programmer by a transmitter in telemetry circuit 38.

Microprocessor 16 receives various status and/or control inputs from pacemaker 15 and defibrillator 17. During normal paceing operations, the input signal to pacemaker 15 is a sense signal on sense line 26 which is used by microprocessor 16 to perform operations such as arrhythmia detection. Microprocessor 16 produces outputs such as the pace control on pace control line 27 which determines the type of pacing to take place. Other pacemaker control outputs generated by microprocessor 16 include a pacing energy control signal on pacing energy control bus 29 which determines the magnitude of the pulse energy, and sensitivity control signal on sensitivity control bus 28, which determines the sensitivity setting of the sensing circuit.

Microprocessor 16 provides to defibrillator 17 a shock control signal on shock control line 32 which indicates that a shock is to be delivered to the patient, a dump control signal on dump control line 34 which indicates that a shock is to be dumped at an internal load within defibrillator 17, and a charge control signal on charge control bus 31 which determines the voltage level of the shock to be delivered. Charged voltage level line 30 provides a digital signal representative of charge voltage from an analog to digital converter within defibrillator 17, thus providing a feedback loop which assures that a shock of proper energy level is delivered by defibrillator 17.

Figure 4:
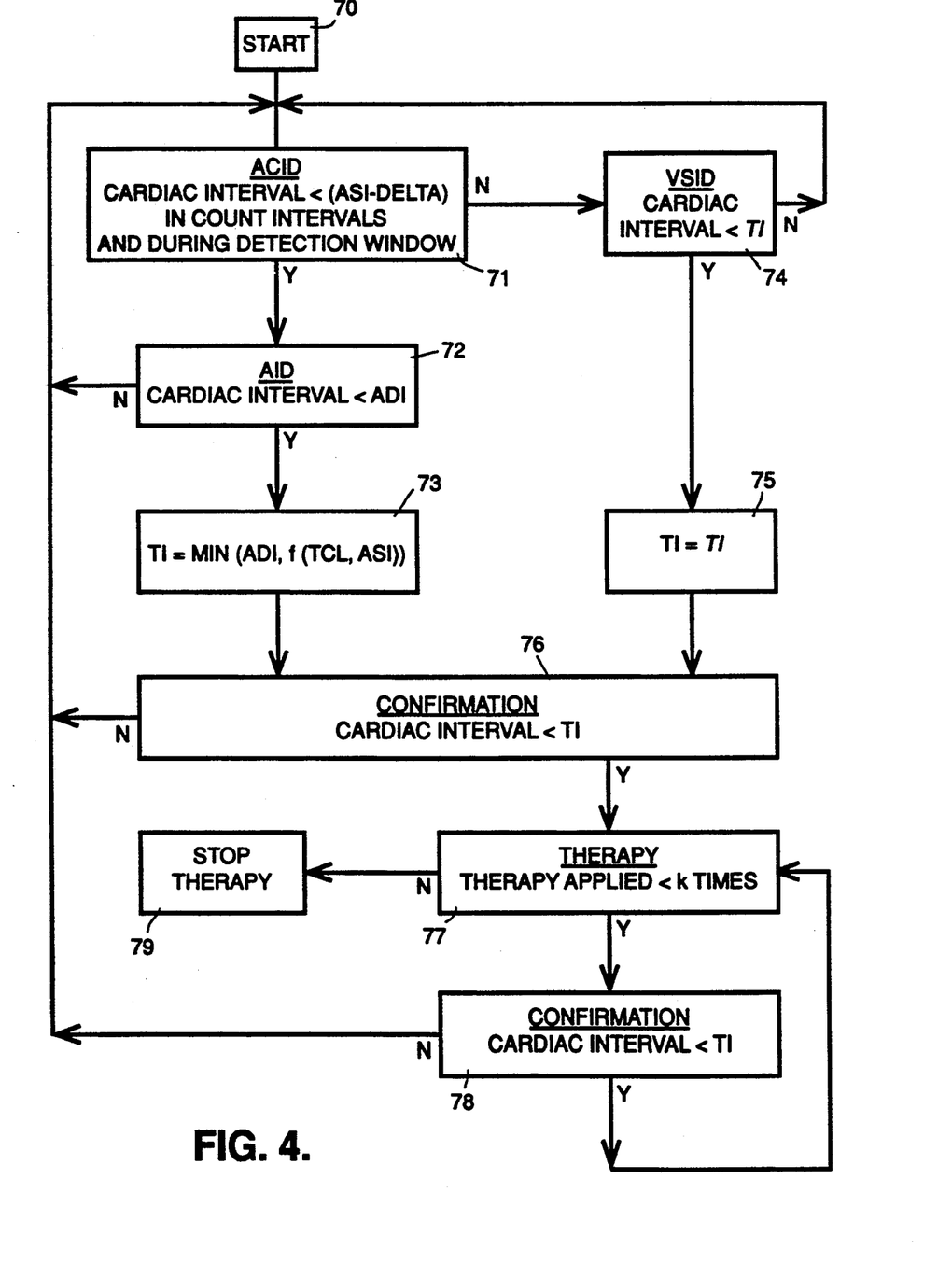
FIG. 4 is a logic diagram of the microprocessor flow control for the detection and confirmation of a tachycardia.

Referring to FIG. 4, there is shown a logic diagram or flowchart of the microprocessor program used for the detection and confirmation of a tachycardia. The start is shown at step 70. At step 71 the ACID algorithm is initiated. The ACID criterion is met if the cardiac interval has decreased by at least an amount DELTA below the average sinus interval (ASI) within a period of time denoted as the count intervals and remains at that level or less for a programmable number of intervals, n, in a period of time denoted as the detection window, where, for example, n=4.

At step 72, the cardiac interval is compared to an Absolute Detection Interval (ADI). If the cardiac interval is less than the ADI, a tachycardia has been detected. The confirmation Threshold Interval (TI) is then determined dynamically at 73 as the minimum of ADI and a value determined by a function of the tachycardia cycle length (TCL) and ASI, that is, TI=min [ADI,f(TCL,ASI)]. In a preferred embodiment, this function f is given by f(TCL,ASI)=TCL+K1×(ASI−TCL), where K1=0.7. If, for example, ADI is programmed at 400 ms and ASI is 385 ms when a tachycardia is detected with a TCL of 300 ms then f(TCL,ASI)=300+0.7×(385−300)=359.5 and TI will be set at TI=min [400,359.5]=359.5 ms.

In another embodiment, the confirmation TI is set to the minimum of ADI and a value determined by a function of the TCL only, that is, TI=min [ADI,f(TCL)] where f(TCL)=K2×TCL and K2=1.2. If, for example, the ADI is programmed at 400 ms when a tachycardia is detected with a TCL of 300 ms, then f(TCL)=1.2×300=360 and TI will be set at TI=min [400,360]=360 ms.

In a further embodiment, the confirmation TI is set to the minimum of the ADI and a value determined by a function of the ASI only, that is, TI=min [ADI,f(ASI)], where f(ASI)=K3×ASI and K3=0.95. If, for example, ADI is programmed at 400 ms and ASI is 385 ms when a tachycardia is detected, then f(ASI)=0.95×385=366 and the TI will be set min[400,366]=366 ms.

If the ACID criterion was not met at step 71, an optional test is made at step 74 for an obvious tachycardia; that is, a tachycardia having a cardiac interval less than that attainable by a sinus tachycardia, using a Very Short Interval Detection (VSID) criterion where at least x out of at most y sensed intervals must be smaller than a detection interval (TI). The parameters x and y are programmable and in a preferred embodiment x=15 and y=18. If the VSID criterion is met, the confirmation interval TI is set to TI at 75 where TI is a programmable parameter and in a preferred embodiment TI=320 ms.

The continued presence of the tachycardia is then confirmed at step 76 using an absolute interval detection (AID) algorithm. The AID criterion is met if at least x out of at most y sensed intervals are smaller than the confirmation interval TI, where x and y are programmable parameters. In a preferred embodiment x=4 and y=4. Following the confirmation of the tachycardia, therapy is applied at step 77. Confirmation is repeated after the delivery of the therapy at step 78. If the tachycardia has not reverted, therapy is again applied. This cycle continues until the tachycardia reverts or until therapy has been applied K times, when therapy is stopped at step 79. The device then enters a passive state in which it remains until the tachycardia terminates, the device is reprogrammed or a magnet is applied.

Figure 5A:
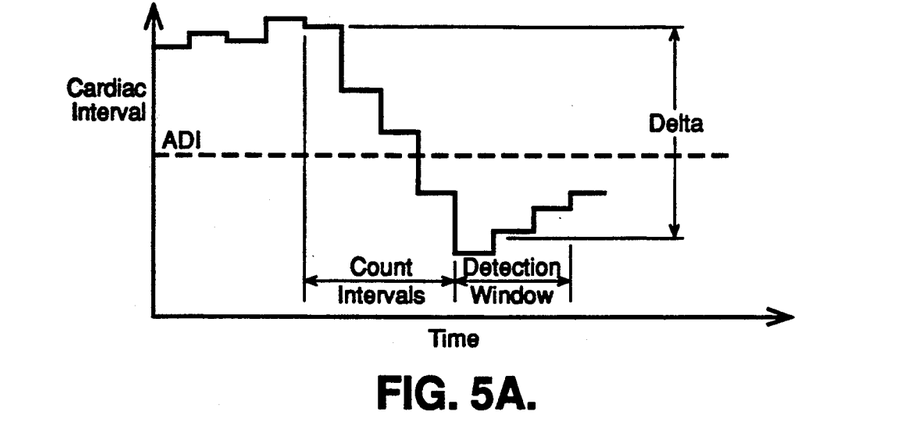
FIG. 5A is a diagram of the cardiac interval during which time the decrease in interval is not sustained for a sufficient number of intervals and ACID is not triggered.

Referring to FIG. 5A, there is shown a diagram of cardiac interval as a function of time during which time the cardiac interval has decreased by at least DELTA from the ASI within the count intervals period. However, this decrease in interval is not sustained for a sufficient number of intervals and hence ACID is not triggered.

Figure 5B:
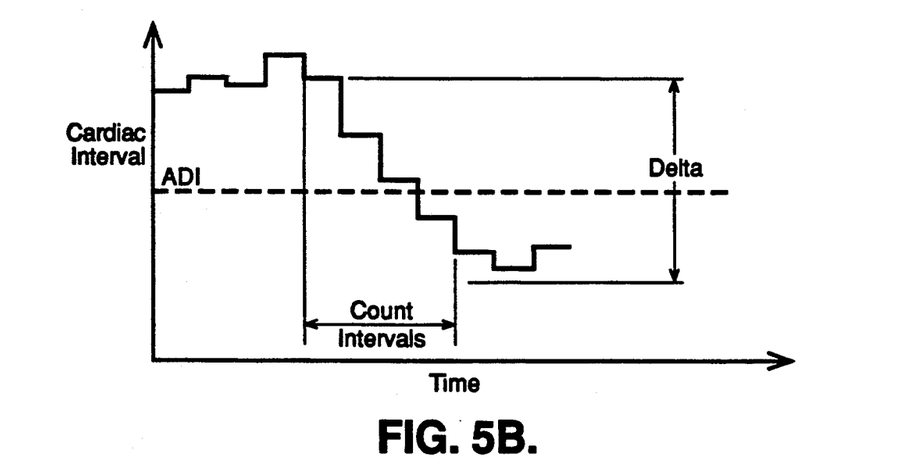
FIG. 5B is a diagram of the cardiac interval during which time the change in interval is less than a predetermined amount and the ACID is not triggered.

In FIG. 5B, the cardiac interval falls below the ADI during the count intervals period. However, the change in interval is less than DELTA as may occur during exercise, and the ACID is not triggered.

Figure 5C:
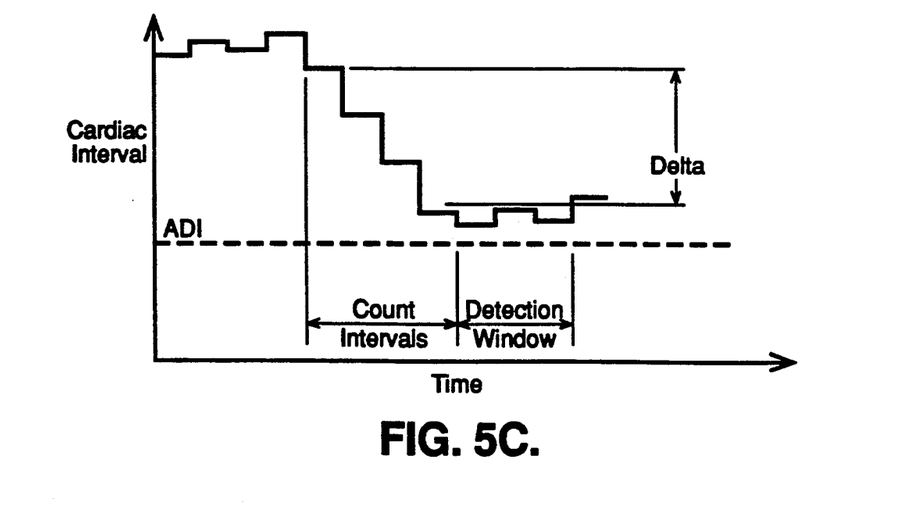
FIG. 5C is a diagram of the cardiac interval during which time the cardiac interval never falls below ADI and a tachycardia is not detected.

In FIG. 5C, the cardiac interval decreases by at least DELTA from ASI within the count intervals period. However, the cardiac interval never falls below the ADI and a tachycardia is not detected.

Figure 6:
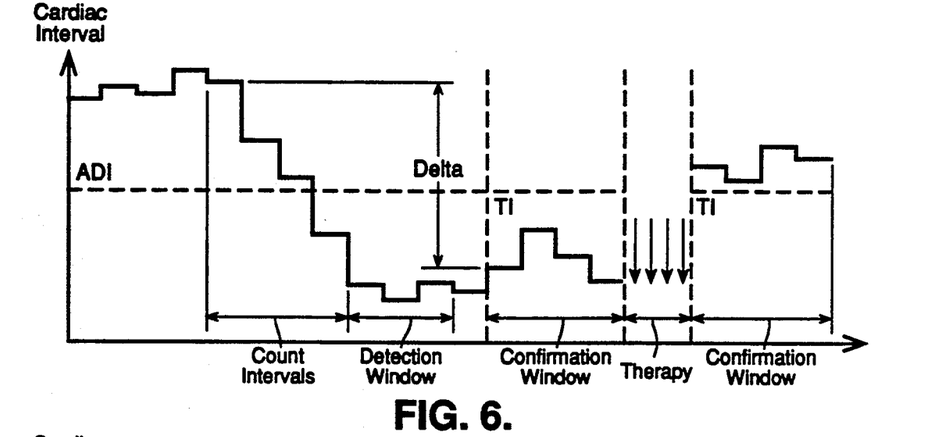
FIG. 6 is a diagram of the cardiac interval during a valid absolute change of interval detection (ACID)

FIG. 6 illustrates cardiac interval as a function of time during positive ACID. The sensed cardiac interval decreases by an amount at least as great as the parameter DELTA from an ASI within the count intervals period, where, for example, DELTA=80 ms and count=4. Because the cardiac interval then remains at that level, or less, for a programmable number of intervals, n, in the detection window and the cardiac interval is less than the ADI, the ACID and AID criteria are met, and the tachycardia is detected.

The AID algorithm is then used to detect the continued presence of the tachycardia prior to the application of therapy. The tachycardia is confirmed as the cardiac interval is less than the confirmation TI, where TI=min [ADI,f(TCL,ASI)]=min[ADI,(TCL+0.7-×(ASI−TCL))]=ADI. After the application of the therapy, confirmation is again performed and the tachycardia is found to have reverted.

Figure 7:
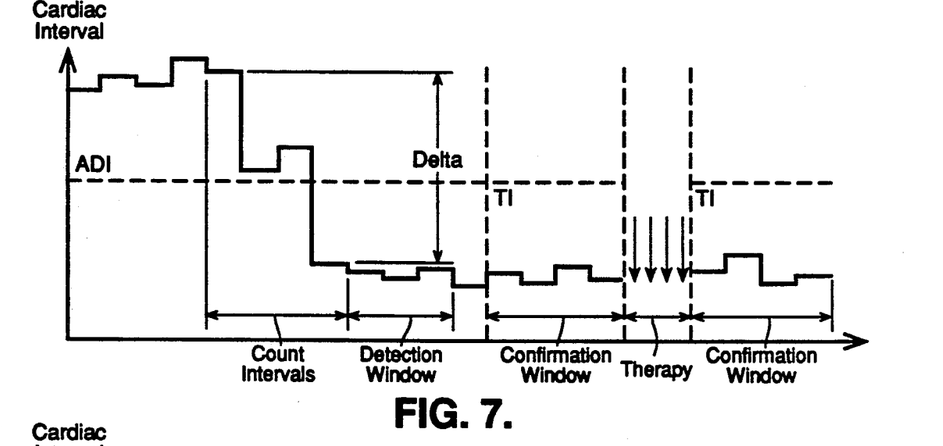
FIG. 7 is a diagram of the cardiac interval during another valid ACID where the change in interval is not monotonic.

FIG. 7 illustrates the cardiac interval as a function of time during another positive ACID. The cardiac intervals need not decrease monotonically throughout the sudden onset window for a tachycardia to be detected. Confirmation of the presence of the tachycardia is again made prior to and after the application of therapy with the TI being determined as in FIG. 6.

Figure 8:
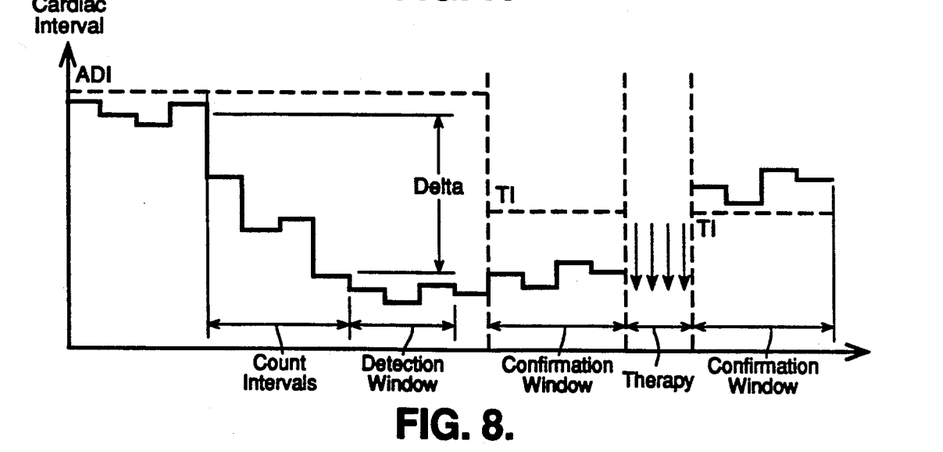
FIG. 8 is a diagram of the cardiac interval during a further valid ACID where the initial cardiac interval is less than the absolute detection interval (ADI).

FIG. 8 illustrates the cardiac interval as a function of time during another positive ACID where the initial cardiac interval is less than the ADI. The sensed cardiac interval decreases by an amount at least as great as DELTA from the ASI within the count intervals period and remains at that level or less for a programmable number of intervals, n, in the detection window, thereby satisfying the ACID criteria.

The AID algorithm is then used to detect the continued presence of the tachycardia prior to the application of therapy. In this instance, the onset of a tachycardia has occurred at an initially decreased cardiac interval such as that which may be reached during exercise. Because the ASI is less than the ADI, TI will be set to a value between the ASI and the TCL as determined by f(TCL,ASI)=(TCL+0.7×(ASI−TCL)).

Confirmation is again performed following the application of therapy. If the ADI had been used for the confirmation threshold, as in prior art devices, successful reversion of the tachycardia would not have been confirmed as the cardiac interval is less than the ADI. However, because the TI has been set to a value between the ASI and the TCL, successful reversion of the tachycardia is recognized due to the cardiac interval being greater than the TI.

Although the invention has been described with reference to a particular embodiment, it is to be understood that this embodiment is merely illustrative of the applications of the principles of the invention. For example, the embodiment described outlines the use of a combination of absolute interval detection and sudden onset detection for differentiating between sinus tachycardias and pathologic tachycardias where the sudden onset detection may be performed by ACID, PCID or other sudden onset algorithms. The invention is disclosed in a combined pacer and cardioverter device. However, it may be applied in devices which are limited in their operation to either antitachycardia pacing or cardioversion therapy.

What is claimed is:

1. An apparatus for determining whether a cardiac tachyarrhythmia exists, comprising:
   absolute change of interval detection means for monitoring a heart;
   absolute interval detection means for evaluating a tachycardia if indicated by said absolute change of interval detection means;
   setting means for setting a confirmation threshold if a tachycardia is indicated by said absolute interval detection means; said confirmation threshold being determined by at least one of an absolute detection interval, tachycardia cycle length, and the average sinus interval of the heart;
   means for comparing cardiac cycle length to the confirmation threshold and for confirming the presence of a tachyarrhythmia if the cardiac cycle length is below the confirmation threshold; and,
   very short interval detection means for detecting a tachyarrhythmia if a tachyarrhythmia is not indicated by said absolute change of interval detection means.

2. The apparatus of claim 1, wherein said very short interval detection means includes comparing means for comparing heart rate to a preprogrammed value to determine whether there is a tachyarrhythmia.

3. The apparatus of claim 2, further comprising means for setting the confirmation threshold to a preprogrammed value if the cardiac interval is less than the preprogrammed value.

4. The apparatus of claim 3, further comprising:
   means for applying antitachyarrhythmia therapy if presence of a tachyarrhythmia is confirmed by said comparing means.

5. The apparatus of claim 4, further comprising:
   means for determining whether the tachyarrhythmia has been reverted after the application of antitachyarrhythmia therapy.

6. The apparatus of claim 5, further comprising:
   means for causing said antitachyarrhythmia therapy to be reapplied if said tachyarrhythmia has not been reverted.

7. An apparatus for determining whether a cardiac tachyarrhythmia exists, comprising:
   absolute change of interval detection means for monitoring a heart;
   absolute interval detection means for evaluating a tachycardia if indicated by said absolute change of interval detection means;
   setting means for setting a confirmation threshold if a tachycardia is indicated by said absolute interval detection means; said confirmation threshold being determined by at least one of an absolute detection interval, tachycardia cycle length, and the average sinus interval of the heart;
   means for comparing cardiac cycle length to the confirmation threshold and for confirming the presence of a tachyarrhythmia if the cardiac cycle length is below the confirmation threshold; and,
   said setting means setting said confirmation threshold as a minimum of the absolute detection interval and a function of the tachycardia cycle length and the average sinus interval.

8. The apparatus of claim 7, comprising means for defining said function as the difference between average sinus interval and tachycardia cycle length and multiplying by a constant; and then adding the tachycardia cycle length.

9. The apparatus of claim 8 wherein said constant is equal to 0.7.

10. An apparatus for determining whether a cardiac tachyarrhythmia exists, comprising:
    absolute change of interval detection means for monitoring a heart;
    absolute interval detection means for evaluating a tachycardia if indicated by said absolute change of interval detection means;
    setting means for setting a confirmation threshold if a tachycardia is indicated by said absolute interval detection means; said confirmation threshold being determined by at least one of an absolute detection interval, tachycardia cycle length, and the average sinus interval of the heart;
    means for comparing cardiac cycle length to the confirmation threshold and for confirming the presence of a tachyarrhythmia if the cardiac cycle length is below the confirmation threshold; and,
    said setting means setting said confirmation threshold as a minimum of the absolute detection interval and a function of the tachycardia cycle length.

11. The apparatus of claim 10, comprising means for defining said function as the tachycardia cycle length multiplied by a constant.

12. The apparatus of claim 11, wherein said constant is equal to 1.2.

13. An apparatus for determining whether a cardiac tachyarrhythmia exists, comprising:
    absolute change of interval detection means for monitoring a heart;
    absolute interval detection means for evaluating a tachycardia if indicated by said absolute change of interval detection means;
    setting means for setting a confirmation threshold if a tachycardia is indicated by said absolute interval detection means; said confirmation threshold being determined by at least one of an absolute detection interval, tachycardia cycle length, and the average sinus interval of the heart;
    means for comparing cardiac cycle length to the confirmation threshold and for confirming the presence of a tachyarrhythmia if the cardiac cycle length is below the confirmation threshold; and, said setting means setting said confirmation threshold as a minimum of the absolute detection interval and a function of the average sinus interval.

14. The apparatus of claim 13, wherein said function is a constant times the average sinus interval.

15. The apparatus of claim 14, wherein said constant is 0.95.

16. An apparatus for treating cardiac arrhythmia comprising:
averaging means for continuously averaging time intervals of a predetermined number of cardiac intervals;
detection means for detecting the presence of a tachycardia;
tachycardia confirmation means for confirming the presence of a tachycardia, said confirmation means including;
calculating means for calculating a value as a function of at least one of average sinus interval determined by said averaging means or tachycardia cycle length; and
threshold setting means for setting a threshold for confirmation to the lesser of said value calculated by said calculating means and an absolute detection interval.

17. The apparatus of claim 16, wherein said function provides a value equal to the sum of:
a) tachycardia cycle length when said detecting means detects a tachycardia; and
b) a constant times the difference between average sinus interval prior to onset of tachycardia and tachycardia cycle length.

18. The apparatus of claim 17, wherein said constant is equal to 0.7.

19. The apparatus of claim 16, wherein said function provides a value equal to a constant times the cardiac cycle length.

20. The apparatus of claim 19, wherein said constant is greater than one.

21. The apparatus of claim 19, wherein said constant is equal to 1.2.

22. The apparatus of claim 16, wherein said function provides a value equal to a constant times the average sinus interval.

23. The apparatus of claim 22, wherein said constant is less than one.

24. The apparatus of claim 22, wherein said constant is equal to 0.95.

25. The apparatus of claim 16, wherein said detection means includes interval means for detecting a sudden change in cardiac interval.

26. The apparatus of claim 25, wherein said interval means is responsive to an absolute change in cardiac interval.

27. The apparatus of claim 25, wherein said interval means is responsive to a percentage change in cardiac interval.

28. The apparatus of claim 16, further comprising:
means for establishing a count interval during which said averaging means averages said time intervals; and
means for establishing a detection window during which said detection means operates.

29. The apparatus of claim 16, further comprising comparing means for comparing cardiac cycle length to a predetermined value to define a tachycardia condition when cardiac cycle length is less than said predetermined value.

30. The apparatus of claim 29, further comprising programming means for programming said predetermined value.

31. The apparatus of claim 29, further comprising storage means for storing a value of said cardiac cycle length when said comparing means has defined a tachyarrhythmia condition.

32. The apparatus of claim 31, wherein said value of said cardiac cycle which has been stored in said storage means is used as tachycardia cycle length by said threshold setting means.

33. The apparatus of claim 16, further comprising absolute interval detection means for comparing average cardiac cycle length to an absolute detection interval to define a tachycardia condition when said average cardiac cycle length is less than said absolute detection interval.

34. A method for determining whether a cardiac tachyarrhythmia exists, comprising the steps of:
a) using absolute change of interval detection to monitor a heart;
b) if a tachycardia is indicated by said absolute change of interval detection, then using absolute interval detection to evaluate said tachycardia;
c) if a tachyarrhythmia is indicated by said absolute interval detection, determining a confirmation threshold in accordance with at least one of an absolute detection interval, tachycardia cycle length and average sinus interval;
d) comparing cardiac cycle length to the confirmation threshold and confirming the presence of tachyarrhythmia if the cardiac cycle length is below the confirmation threshold.

35. The method of claim 34, wherein if no tachycardia is indicated by said absolute interval detection, then considering that there is no tachycardia.

36. The method of claim 34, further comprising the step of using very short interval detection to evaluate the tachycardia, if a tachycardia is not indicated by said absolute change of interval detection.

37. The method of claim 36, wherein said step of using very short interval detection comprises comparing heart rate to a preprogrammed value.

38. The method of claim 37, wherein if cardiac interval is greater than the preprogrammed value, it is determined that there is no tachyarrhythmia.

39. The method of claim 37, wherein if cardiac interval is less than the preprogrammed value, the confirmation threshold is set to said preprogrammed value.

40. The method of claim 39, further comprising the step of:
e) applying antitachyarrhythmia therapy if tachycardia is confirmed at step d).

41. The method of claim 40, further comprising the step of:
f) again confirming if a tachycardia exists in the manner of step d).

42. The method of claim 41, further comprising repeating steps e) and f) until the tachyarrhythmia has been reverted or until antitachycardia therapy has been applied k times, where k is an integer.

43. The method of claim 34, further comprising the step of:
e) applying antitachyarrhythmia therapy if tachycardia is confirmed at step d).

44. The method of claim 43, further comprising the step of:

f) again confirming if a tachycardia exists in the manner of step d).

45. The method of claim 44, further comprising repeating steps e) and f) until the tachyarrhythmia has been reverted or until antitachycardia therapy has been applied k times, where k is an integer.

46. The method of claim 34 wherein said confirmation threshold is determined as a minimum of the absolute detection interval and a function of the tachycardia cycle length and the average sinus interval.

47. The method of claim 46 wherein the function is computed by taking a difference between average sinus interval and tachycardia cycle length and multiplying by a constant and then adding the tachycardia cycle length.

48. The method of claim 47 wherein the constant is equal to 0.7.

49. The method of claim 34 wherein said confirmation interval is determined as a minimum of the absolute detection interval and a function of the tachycardia cycle length.

50. The method of claim 49 wherein said function is computed by multiplying the tachycardia cycle length by a constant.

51. The method of claim 50 wherein the constant is equal to 1.2.

52. The method of claim 34 wherein said confirmation interval is determined as a minimum of the absolute detection interval and a function of the average sinus interval.

53. The method of claim 52 wherein said function is a constant times average sinus interval.

54. The method of claim 53 wherein said constant is 0.95.

55. A method for detecting tachyarrhythmia comprising the steps of:
averaging the length of a predetermined number of cardiac intervals;
detecting the presence of a tachycardia based on a change in length of cardiac interval;
determining a value as a function of at least one of average sinus interval found by said step of averaging and tachycardia cycle length;
setting a threshold for confirmation to the lesser of said value determine by said function and an absolute detection interval; and,
confirming the presence of a tachycardia if the cardiac interval is below said threshold.

56. The method of claim 55 wherein said function provides a value equal to the sum of:
a) tachycardia cycle length when a tachycardia is detected; and
b) a constant times the difference between average sinus interval prior to onset of tachycardia and tachycardia cycle length.

57. The method of claim 56, wherein said constant is equal to 0.7.

58. The method of claim 55, wherein said function provides a value equal to a constant times the cardiac cycle length.

59. The method of claim 58, wherein said constant is greater than one.

60. The method of claim 58, wherein said constant is equal to 1.2.

61. The method of claim 55, wherein said function provides a value equal to a constant times the average sinus interval.

62. The method of claim 61, wherein said constant is less than one.

63. The method of claim 61, wherein said constant is equal to 0.95.

64. The method of claim 55, wherein said step of detection includes detecting a sudden change in cardiac interval.

65. The method of claim 64, wherein said step of detection includes detecting an absolute change in cardiac interval.

66. The method of claim 64, wherein said step of detection includes detecting a percentage change in cardiac interval.

67. The method of claim 55, further comprising the steps of:
establishing a count interval during which said step of averaging occurs; and
establishing a detection window during which said step of detecting occurs.

68. The method of claim 55 further comprising comparing cardiac cycle length to a predetermined value to define a tachyarrhythmia condition when cardiac cycle length is less than said predetermined value.

69. The method of claim 68, further comprising the steps of
storing said predetermined value; and
using said stored value to set said threshold.

70. The method of claim 55, further comprising the step of using absolute interval detection for comparing average cardiac cycle length to an absolute detection interval to define a tachycardia condition when said average cardiac cycle length is less than said absolute detection interval.

71. A method of treating cardiac arrhythmias comprising the steps of:
detecting the presence of a tachycardia by means of sudden onset detection and an absolute detection interval;
measuring the tachycardia cycle length of said detected tachycardia;
delivering antachycardia therapy responsive to said detecting to revert said tachycardia;
confirming the presence of said tachycardia according to the level of a threshold interval;
determining a function of said tachycardia cycle length;
setting said threshold interval to the lesser value of said function and said absolute detection interval; and
delivering further antitachycardia therapy responsive to said confirming.

72. The method according to claim 71, wherein said sudden onset detection is performed by absolute change of interval detection.

73. The method according to claim 71, wherein said sudden onset detection is performed by percentage change of interval detection.

74. The method according to claim 71, wherein said tachycardia confirming occurs after said delivering of antitachycardia therapy.

75. The method according to claim 74, wherein said tachycardia confirming also occurs at least once before said delivering of antitachycardia therapy.

76. The method according to claim 71, wherein said detecting is also performed by very short interval detection for the purpose of detecting pathologic tachycardias whose cardiac intervals are less than those attainible by sinus tachycardias.

* * * * *